United States Patent [19]

Baertschi

[11] Patent Number: 5,043,321
[45] Date of Patent: Aug. 27, 1991

[54] ADRENOCORTICOTROPIN RELEASE INHIBITING FACTOR

[75] Inventor: Alex J. Baertschi, Charlottesville, Va.

[73] Assignees: Center for Innovative Technology, Herndon; University of Virginia, Charlottesville, both of Va.

[21] Appl. No.: 217,237

[22] Filed: Jul. 11, 1988

[51] Int. Cl.$^5$ .............................................. A61K 37/02
[52] U.S. Cl. ...................................... 514/12; 514/805
[58] Field of Search ................... 514/2, 12, 13, 14, 15, 514/16, 17, 18, 805

[56] References Cited

U.S. PATENT DOCUMENTS

| | | | |
|---|---|---|---|
| 4,605,642 | 8/1986 | Rivier et al. | 530/324 |
| 4,607,023 | 8/1986 | Thibault et al. | 514/324 |
| 4,643,989 | 2/1987 | Baird | 514/12 |
| 4,663,437 | 5/1987 | de Bold | 530/324 |

OTHER PUBLICATIONS

Rudinger, Peptide Hormones, Parsons (Ed.), U. Park Press, Baltimore, pp. 1–7, (1976).
Talmadge et al., 13th International Congress of Chemotherapy, Spitzy et al., (Ed.) Proceedings, pp. 203/19–203/35 (1983).
Takao et al., Life Sciences, vol. 42, pp. 1199–1203 (1988).
Anand-Srivastava et al., Life Sciences, vol. 36, pp. 1873–1879 (1985).
King et al., Soc Neurosci Abstr 14(2), p. 1285 (1988).
Vale et al., Science, vol. 213, pp. 1394–1397, (1981).
Atlas et al., Ann. Rev. Med., vol. 37, pp. 397–414 (1986).
Ballerman et al., Cir. Res. vol. 58, pp. 619–630 (1986).
Grenest et al., Circulation, vol. 75, pp. 1118–124 (1/87).
Peninsula Labs. Catalog, pp. 1, 31–33, Belmont, California, (1990–1991).
R. Hashimoto et al., Regulatory Peptides, 17:53 (1987).
S. Baertschi et al., Int. Cong. Neuroendocrin., San Francisco (1987).
T. Abou-Samra et al., Endocrinology, 120:18 (1987).
U. Heisler et al., Mol. Cell. Endocrinol., 44:125 (1986).
V. Simard et al., Regulatory Peptides, 15:269 (1986).
W. Shibasaki et al., Biochem. Biophys. Res. Comm., 135:1035 (1986).
X. Hattori et al., Endocrinol. Japan., 33:533 (1986).
Y. Okajima et al., Horm. Metab. Res. 18:497 (1986).
Z. Rosenthal et al., Life Sciences, 40:1179 (1987).
Z. Graham et al., Atrial Natriuretic Factor, Chapter 65 (1987).

*Primary Examiner*—Lester L. Lee
*Assistant Examiner*—Christina Chan
*Attorney, Agent, or Firm*—Whitham & Marhoefer

[57] ABSTRACT

A method for alleviating stress induced immunosuppression is accomplished by application of low doses of ANF[1-28] or other ANF analogs having intact N-terminal sequences. Atrial natriuretic factors (ANFs) with intact N-terminal sequences are shown to be effective inhibitors of CRF 41-stimulated ACTH secretion when the ANFs are present in low concentrations. ANF[1-28] significantly inhibited ACTH release stimulated by 1–5 nM CRF. At the most effective concentration of 100 pM, ACTH release was inhibited by 40.1% ($p<0.001$). This effect was manifested after three hours, but not after only one half or one hour of incubation. Conversely, ANF[5-28], at concentrations of 10 to 10,000 pM, had no effect on ACTH secretion after one half, one, or three hours. ANF[1-11] weakly inhibited ACTH secretion at concentrations of 100 pM and 1000 pM. Again, three hours of incubation was required to manifest these effects.

1 Claim, 5 Drawing Sheets

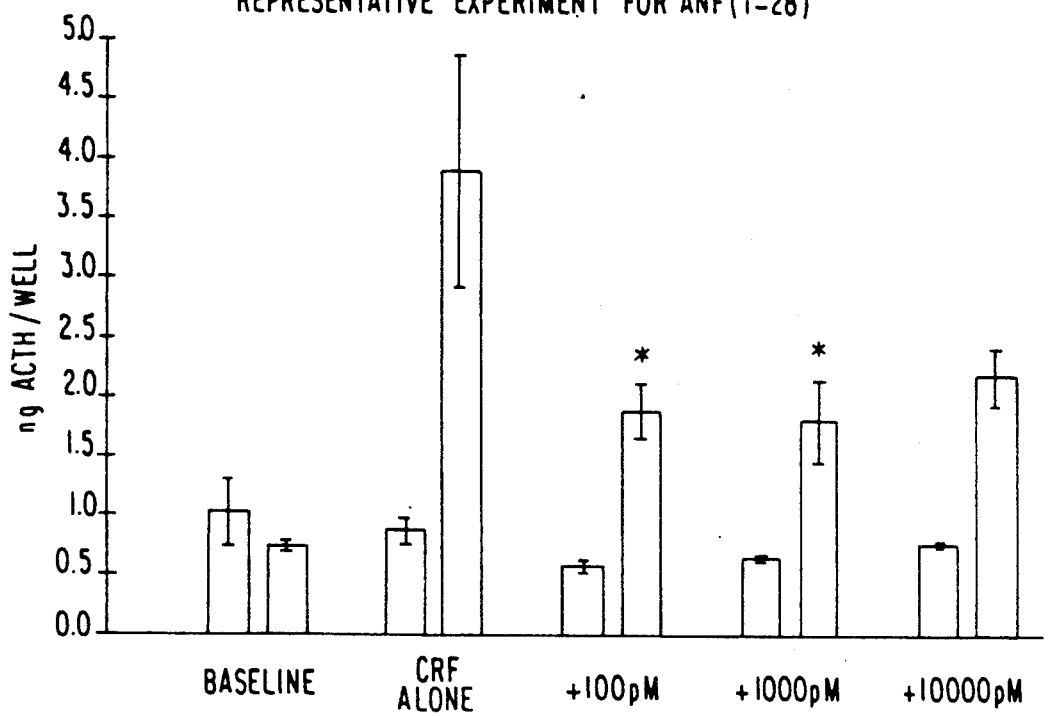
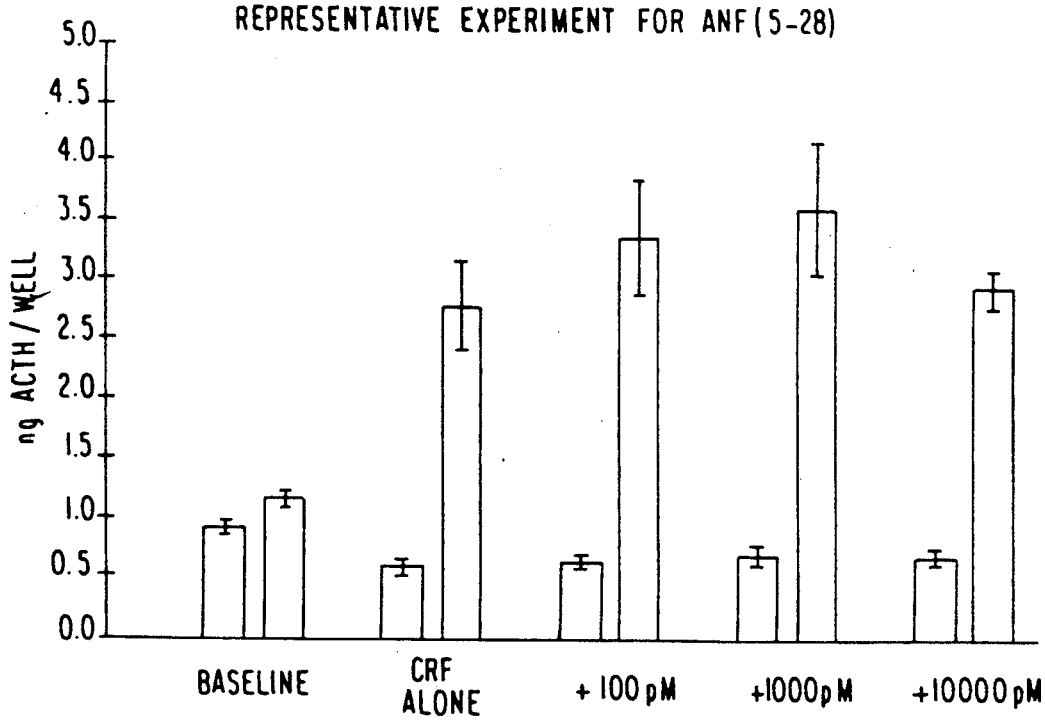

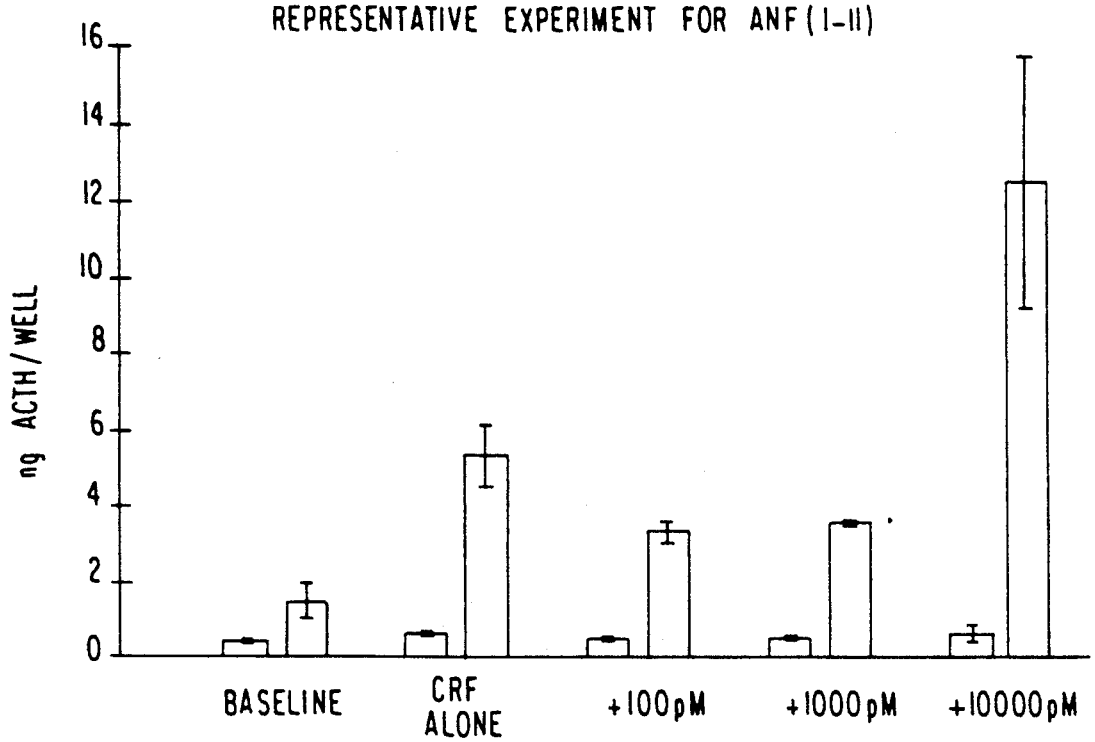
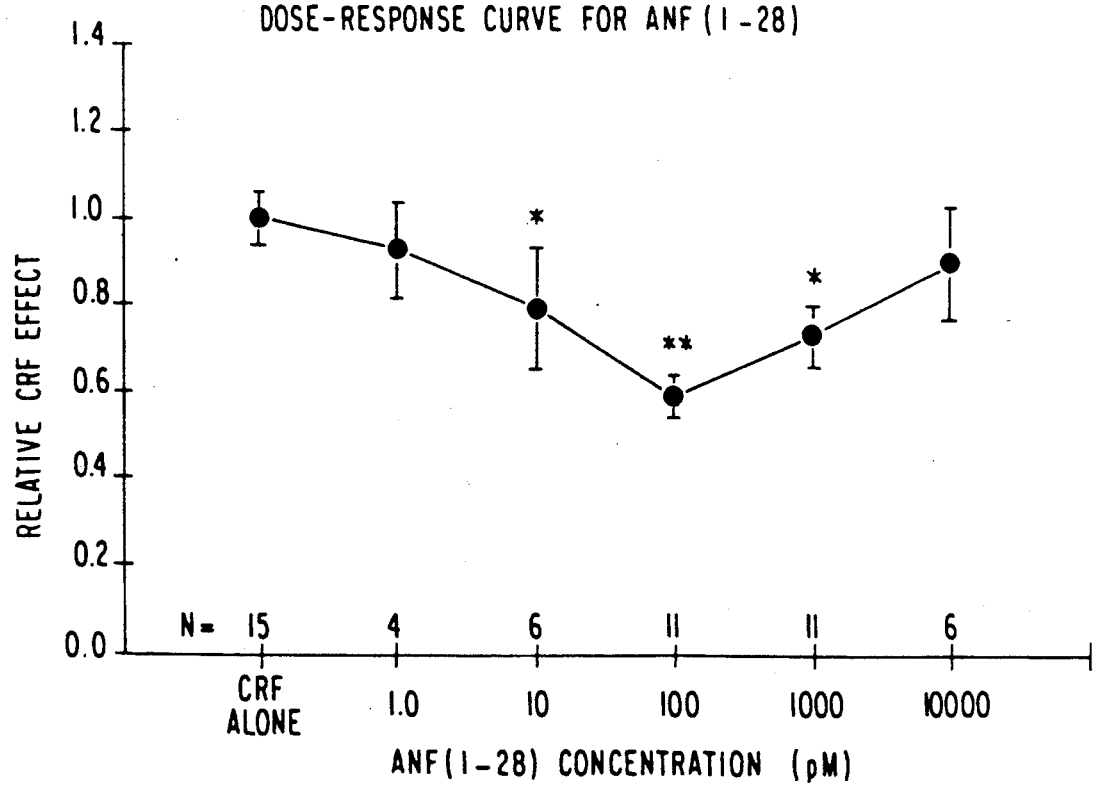

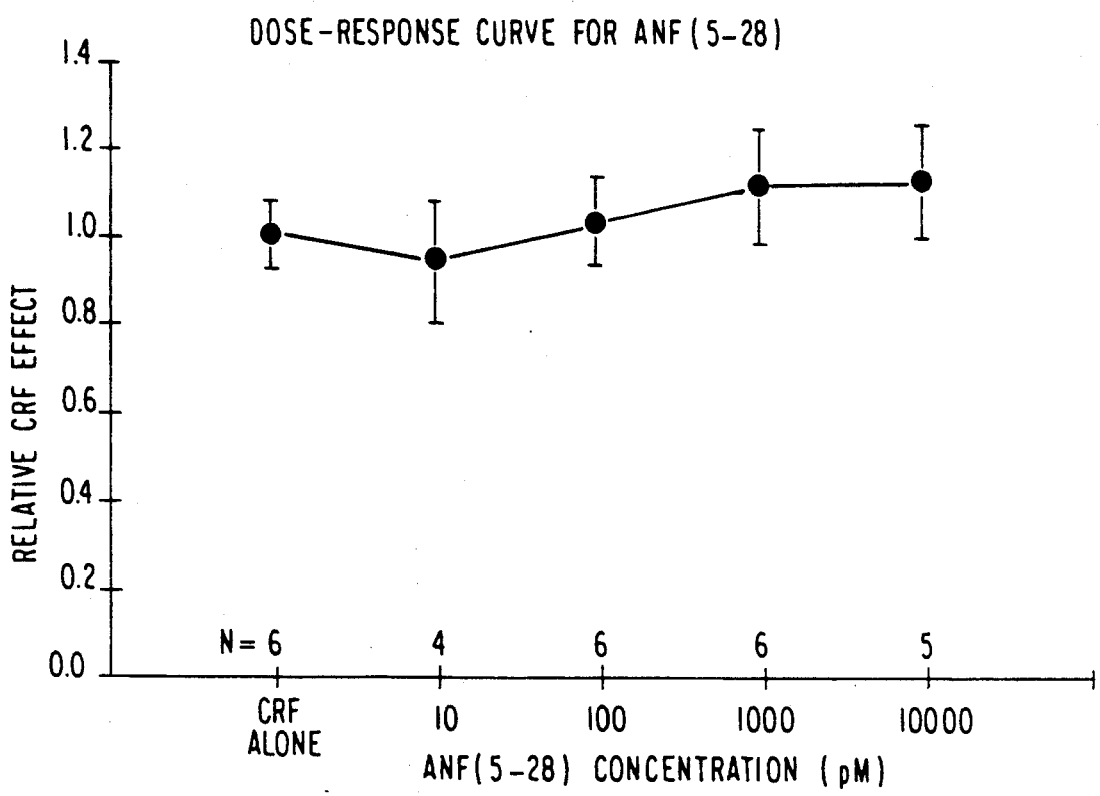
FIG.5 DOSE-RESPONSE CURVE FOR ANF(5-28)
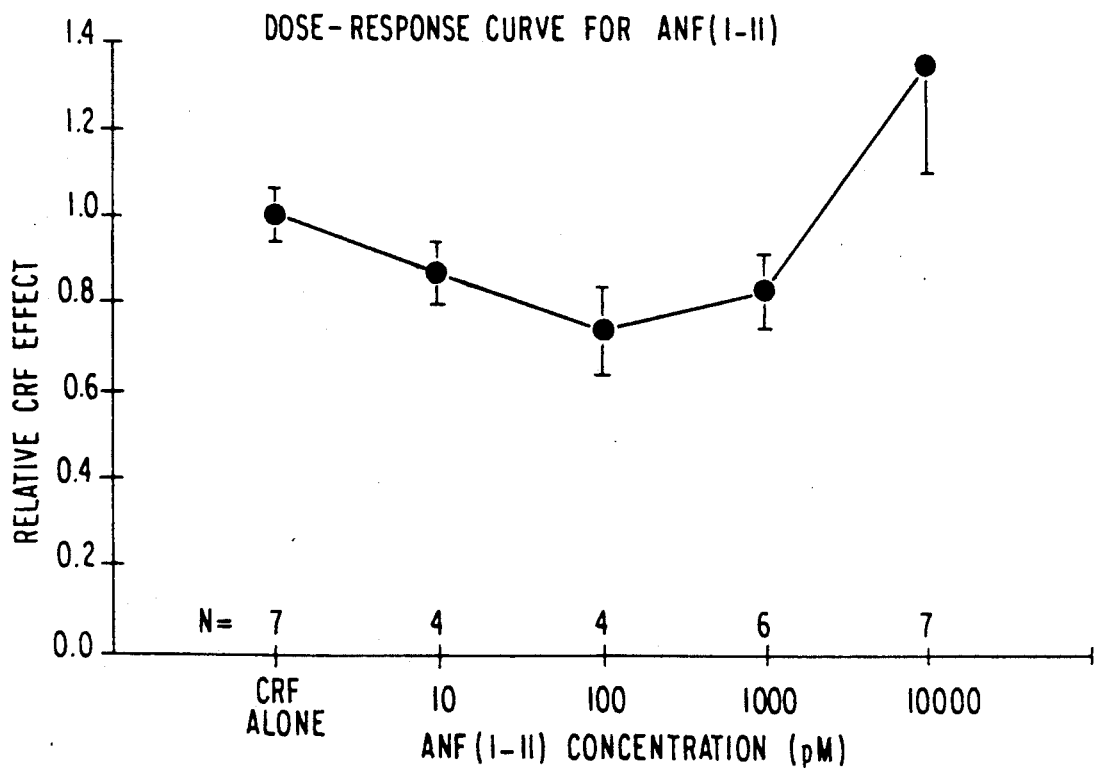
FIG.6 DOSE-RESPONSE CURVE FOR ANF(1-11)

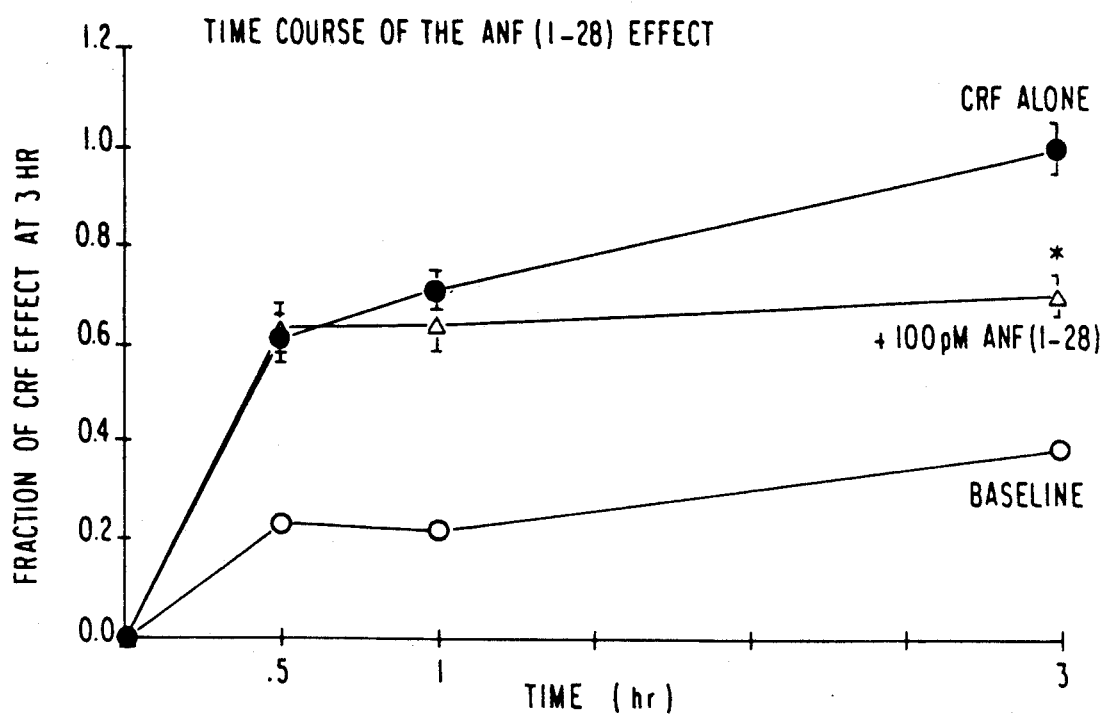
FIG. 7 TIME COURSE OF THE ANF(1-28) EFFECT
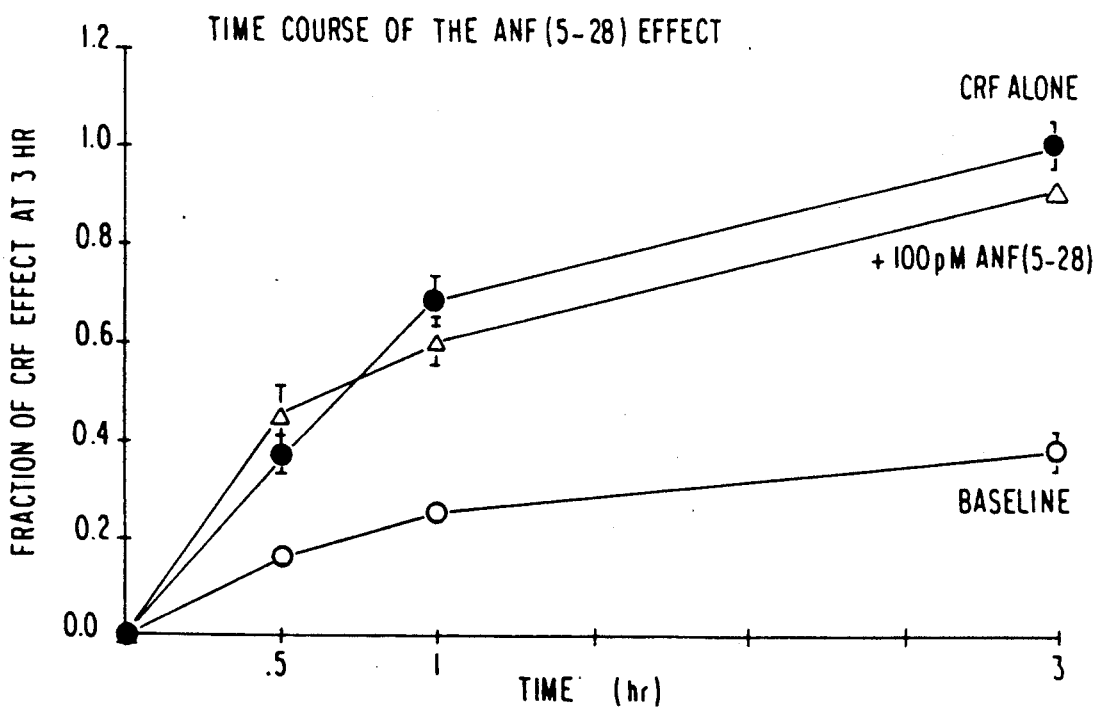
FIG. 8 TIME COURSE OF THE ANF(5-28) EFFECT

ADRENOCORTICOTROPIN RELEASE INHIBITING FACTOR

BACKGROUND OF THE INVENTION

1. Field of the Invention

The present invention generally relates to a method of inhibiting adrenocorticotropin (ACTH) secretion and, more particularly, to using an atrial natriuretic factor (ANF) with an intact N-terminal sequence to inhibit corticotropin releasing factor (CRF 41) induced ACTH secretion.

2. Description of the Prior Art

Current research suggests that the brain pituitary adrenal cascade of stress hormones may mediate stress induced disease in humans and animals. Partial immunosuppression, one of the proposed mechanisms, may increase the susceptibility to infectious disease and lead to tumor development; therefore, an inhibitor of inappropriate stress hormone secretion during psychological and emotional stress may find widespread use in preventive medicine. In addition, stress hormone inhibitors may be useful in animal husbandry because excessive release of stress hormones may lead to stunted growth in domestic animals.

ANF is a family of polypeptides, all of which have a common amino acid sequence, but differ in length by the presence or absence of 1–8 amino acids on the amino or carboxyl termini (N-terminal or C-terminal, respectively). ANF peptides are bio-active hormonal substances which are synthesized in cardiac atria. U.S. Pat. No. 4,663,437 to de Bold discloses that extracts of ANF peptides play a role in extracellular fluid volume regulation. Shortly after administration, the extract enhances urinary flow and increases urinary sodium, potassium, and chloride excretion. U.S. Pat. No. 4,607,023 to Thibault et al discloses synthesized ANF peptides having diuretic, natriuretic, vasorelaxant, hypotensive or antihypertensive properties. These synthesized ANF peptides are administered systemically, either by intravenous, subcutaneous, or intramuscular injection, or by sublingual or nasal administration.

U.S. Pat. No. 4,643,989 to Baird discloses atrial peptides, which are ANF-like polypeptides, that inhibit aldosterone secretion. These peptides or pharmaceutically acceptable salts thereof, dispersed in a pharmaceutically acceptable liquid or solid, can be administered to mammals in order to inhibit basal aldosterone secretion and thereby manage aldosterone dependent hypertension.

The secretion of ACTH is ultimately controlled by the hypothalamus. In response to stress situations, the hypothalamus secretes CRF which is sent to the anterior pituitary and stimulates it to release ACTH into the blood. ACTH binds to receptors on cells of the adrenal cortex, stimulating the production of steroid hormones, which are mainly cortisol (in humans) and corticosterone (in rats). To date, there is no generally accepted ACTH-release inhibitor.

U.S. Pat. No. 4,605,642 to Rivier et al discloses polypeptide analogs that are competitive antagonists of CRF 41 in mammals. These antagonists or pharmaceutically acceptable salts thereof, dispersed in a pharmaceutically acceptable liquid or solid carrier, can be administered to mammals, including humans, to prevent the elevation of ACTH. They may be used to affect mood, memory and learning, as well as diagnostically. In an article by the same inventors, alpha helical ovine CRF 9-41 was shown to blunt stress induced ACTH release in non-anesthetized rats (see, Rivier et al, *Science* 224, pp. 889–891 (1984)). However, very high concentrations (micromolar) are required to block CRF 41 induced ACTH secretion. Moreover, CRF 9-41 is a large peptide which is costly to produce in large quantities and is difficult to introduce into the blood stream by non-invasive means.

Okajima et al have disclosed that delta sleep inducing peptide (DSIP) inhibits CRF induced ACTH secretion from the rat anterior pituitary gland in vitro (see, Okajima et al, *Horm. Metab. Res.* 18, pp. 497–498 (1986)). Okijima et al found that 10 nanomolar (nM) DSIP was the most effective concentration for inhibition of ACTH secretion. It is difficult and costly to maintain such high concentrations of peptides in the blood stream because of their short half life due to enzymatic cleavage.

SUMMARY OF THE INVENTION

It is an object of this invention to provide a method of inhibiting CRF 41 induced ACTH secretion by using an ANF peptide at low concentrations and with an intact N-terminal sequence.

It is another object of this invention to provide a method for alleviating stress induced immunosuppression by application of low doses of ANF[1-28] as well as other ANF analogs having intact N-terminal sequences.

According to the invention, low concentrations of ANF[1-28] and ANF[1-11] were found to inhibit ACTH secretion in vitro, while ANF[5-28] was found to have no effect on CRF 41 induced ACTH secretion. CRF 41 was discovered in 1981 and is the most active hormone stimulator of ACTH secretion. The number 41 simply identifies the number of amino acids in the peptide. Other active factors such as CRF 41-like polypeptides which have significant homology with CRF 41, are considered within the scope of this invention.

ANF peptides were recently detected in the hypothalamus of the rat. ANF analogs can be described as any peptide having significant homology with any part of the ANF amino acid sequence, and pharmaceutically acceptable salts, sugars, esters and amides thereof. Nuclei involved in the regulation of anterior pituitary hormone secretion contain cells immunoreactive for ANF, suggesting that ANF may modulate pituitary hormone release. Consistent with this hypothesis, ANF-like substances have been shown to be released from rat hypothalamic fragments in vitro (see, Shibasaki et al, *Biochem. Biophys. Res. Commun.* 136, pg 590, (1986)), to bind to anterior pituitary cells (see, Quiron, *Peptides* 5, pg. 1167, (1984) and Kurihara, *Brain Res.* 408, pg. 31 (1987)), to increase cyclic guanosyl monophosphate (cGMP) (see, Abou-Samra, *Endocrinology* 120, pg. 18, (1987), Heisler, *Mol. Cell Endocrinol.* 44, pg. 125, (1986), and Simard, *Regulatory Peptides* 15, pg. 269 (1986)), and possibly to decrease cyclic adenosyl monophosphate (cAMP) (see, Anand-Srivastava, *Life Sci.* 36, pg. 1873, (1985)). However, these effects were not linked to hormone release.

Several investigators have reported that ANF does not modulate ACTH secretion; however, their seemingly controversial results can be explained by the inventor's recent experimental work where the inhibitory effects were only evident under the following three conditions: first, prolonged test periods must be used (up to 3 hours (3 h); second, low concentrations of ANF must be present (0.01 nM to 0.1 nM); third, the ANF analog used must have an intact N-terminal sequence. Heisler et al demonstrated that 100 nM ANF[3-28] (or ANF[8-33]) did not affect ACTH release after three hours of incubation (see, Heisler, *Mol. Cell Endocrinol.* 44, pg. 125, (1986)). The inventor showed that a one to two hour incubation with 50 nM ANF[1-28] was ineffective at altering ACTH secretion in culture (see, Baertschi et al, *1st Intl. Con. Neuroendocrinol.*, (1986)). Hashimoto et al used an unidentified ANF form, at high concentrations (3-300 nM) and found no effect on ACTH release after three hours (see, Hashimoto et al, *Regulatory Peptides* 17, pg 53, (1987)). Abou-Samra et al obtained similar results using 100 nM ANF[5-28] (see, Abou-Samra, *Endocrinology* 120, pg. 18, (1987)).

In contrast, Shibasaki et al found that relatively low concentrations (0.01-1 nM) of ANF[4-28] inhibits basal and CRF 41 stimulated ACTH release in vitro by less than 10% (see, Shibasaki et al, *Biochem. Biophys. res. Commun.* 135, pg 1035, (1986)). However, negligibly low levels of CRF 41 stimulation were used in the studies (0.1-1 picomolar (pM)) calling into question the effects which were observed. At least 100 times more CRF 41 would be required to stimulate the release of ACTH and the inventor used 1000 times more (1 nM to 5 nM) in his investigations. It is more difficult to inhibit ACTH secretion at greater concentrations of CRF and; therefore, data obtained at greater concentrations is more reliable. Hattori et al showed that alpha-hANP (presumably ANF[1-28]) had no effect on hemorrhage induced corticosterone secretion in vivo, although their preliminary study suggests, paradoxically, an inhibition of plasma ACTH that was not dose dependent (see, Hattori et al, *Endocrinol. Japon.* 33, pg 533, (1986)). The observation of no effect on corticosterone secretion is inconsistent with the effect on ACTH secretion, since many investigators have shown that corticosterone levels in plasma are reflected by ACTH levels.

Previous experiments which show the lack of an effect of ANF on ACTH release may have been due to the use of relatively high concentrations or truncated forms of ANF. The inventor utilized various molecular forms and a wide range of concentrations of ANF to re-examine its effect on CRF-stimulated ACTH release from cultured anterior pituitary cells. The inventor has found that only low concentrations of ANF analogs with intact N-terminal sequences will inhibit CRF 41 induced ACTH secretion and that three hours of incubation are required to demonstrate this inhibition in culture.

It is common knowledge that ACTH is part of a large precursor protein. That precursor protein releases many bioactive peptides, such as alpha-MSH, beta-MSH, beta-endorphin, and beta-LPH, upon stimulation by CRF 41 in conjunction with the release of ACTH. In consequence, inhibition of ACTH release by ANF-[1-28] or other ANF analogs with intact N-terminal sequences will cause inhibition of these peptides. Both cortisol, which is released in response to ACTH, and beta-endorphin have been shown to cause partial immunosuppression. Therefore, low doses of ANF analogs with intact N-terminal sequences should alleviate stress induced immunosuppression. These ANF analogs are at least 100 times more potent than DSIP and CRF 9-41 and are easier to produce than CRF 9-41. It is anticipated that the ANF analogs can be administered non-invasively by nasal inspiration, buccal application for intestinal absorption, by suppository, by injection or other means.

BRIEF DESCRIPTION OF THE DRAWINGS

The foregoing and other objects, aspects and advantages of the invention will be better understood from the following detailed description of the preferred embodiments of the invention with reference to the accompanying drawings, in which:

FIG. 1 is a bar graph showing representative results obtained from an experiment with ANF[1-28] at varying concentrations and showing that ANF[1-28] at 100 pM significantly suppressed the CRF induced release of ACTH;

FIG. 2 is a bar graph showing representative results obtained from an experiment with ANF[5-28] at varying concentrations and showing that ANF[5-28] does not suppress CRF induced release of ACTH;

FIG. 3 is a bar graph showing representative results obtained from an experiment with ANF[1-11] at varying concentrations and showing that ANF[1-11] at concentrations less than 1000 pM have a suppressing effect on CRF induced release of ACTH;

FIG. 4 is a line graph comprised of data points obtained from fifteen experiments performed in accordance with procedures used for FIG. 1 and showing a dose response curve where different concentrations of ANF[1-28] plus CRF 41 have varying relative CRF effects;

FIG. 5 is a line graph comprised of data points obtained from six experiments performed in accordance with the procedures used for FIG. 2 and showing a dose response curve where different concentrations of ANF-[5-28] plus CRF 41 have similar relative CRF effects;

FIG. 6 is a line graph comprised of data points obtained from seven experiments performed in accordance with the procedures used for FIG. 3 and showing a dose response curve where different concentrations of ANF[1-11] plus CRF 41 have varying relative CRF effects;

FIG. 7 is a line graph showing the suppressive effect of ANF[1-28] on CRF 41 induced ACTH release over a period of time;

FIG. 8 is a line graph showing the lack of effects of ANF[5-28] on CRF 41 induced ACTH release over a period of time.

DETAILED DESCRIPTION OF THE PREFERRED EMBODIMENT OF THE INVENTION

Figure 9:
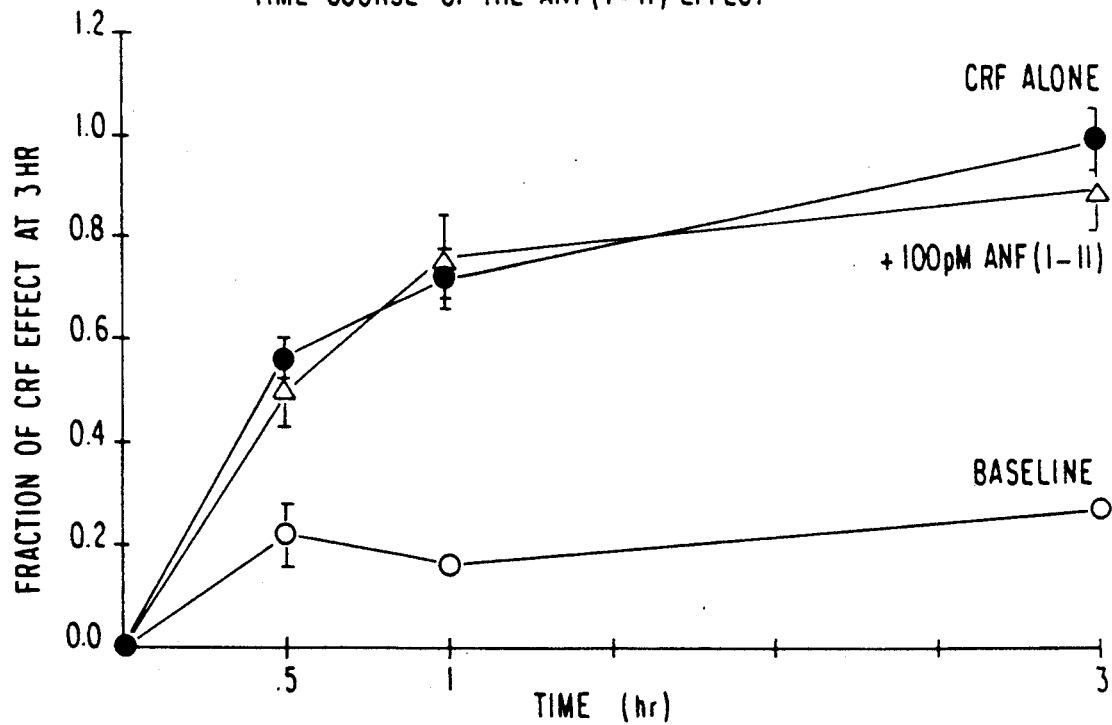
FIG. 9 is a line graph showing the effect of ANF-[1-11] on CRF 41 induced ACTH release over a period of time.

Referring now to the drawings and, more particularly to FIGS. 1, 2, and 3, which show representative results obtained from experiments performed with ANF[1-28], ANF[5-28], and ANF[1-11], respectively, the materials and methods employed are outlined as follows:

(1) Cell Culture: Before decapitation, female Sprague-Dawley rats obtained from the Dominion company of Dublin, Va., weighing between 240-300 grams were anesthesized with halothane, available from Halocarbon Laboratories of Hackensack, N.J. Immediately following decapitation, the pituitary anterior lobes were removed and placed into sterile RPMI medium, which is available from Gibco of Grand Island, N.Y., supplemented with 18.9 micrograms/milliliter ($\mu$g/ml)

penicillin, 7.5 μg/ml streptomycin, 0.56 μg/ml amphotericin B, 15 μg/ml gentamycin, and 7.5% fetal calf serum (Gibco), 2.5% horse serum (Gibco), 2 mg/ml sodium bicarbonate ($NaHCO_3$) available from the Sigma Corporation of Saint Louis, Mo., at pH 7.4 and 37° C., and minced into small pieces. The pieces were washed in serum free RPMI and then digested with trypsin, available from the Worthington Biochemic Company of Freehold, N.J., at 20 mg/10 ml for twenty to thirty minutes at 37° C. After inactivation of the trypsin with 10% horse serum, the pieces were mechanically dispersed into cells by repeated pipetting with a 1 ml pipet tip, available from the Rainin company of Woburn, Mass. The cells were counted and the viability was assessed by trypan blue exclusion. Viability was found to be 89% with a 1% error margin. The cells were then transferred to twenty four well culture plates, available from Falcon Primara of Oxnard, Calif., at a density of 455,000±27,310 cells/well (mean±SEM) and grown in RPMI medium containing serum (as above). The cells were incubated at 37° C. in a 5% carbon dioxide ($CO_2$)-95% air mixture and fed, on the first and third days of culture, by addition or replacement of medium.

(2) Experimental Protocol: All experiments were conducted on cells that had been in culture four days. The cells were first washed three times for ten minutes in an experimental buffer comprised of RPMI from Gibco, HEPES at 0.6mg/ml from Sigma, 1% bovine serum albumin from Sigma, 50 micromolar (μM) ascorbic acid from Sigma, at pH 7.4 and an osmolality of 290 mOsm/kg. The cells were then incubated in this buffer for one to three hours to assess the baseline secretion rate of each well as shown by the first bar of each pair of bars in FIGS. 1, 2, and 3. During this time, dilutions of CRF 41, between 1 and 5 nM, and dilutions of ANF peptides, between 1 and 10,000 pM, were made in cold buffer (5° C.) which was warmed to 37° C. immediately before use. With each group consisting of four wells, the peptides were added in various combinations as indicated in the results. In some experiments, all wells were incubated with buffer subsequent to the test period to re-assess the baseline secretion. In most experiments two groups received CRF 41 alone to determine a maximal response with a total of eight wells (for statistical purposes). The initial volume added to each well, at the beginning of the test period, was 300 microliters (μl). To avoid mechanical disturbance of the cells, only 30 μl of buffer was removed at each time point (0.5, 1, and 3 hours) without replacement. The samples were immediately diluted in ratios of 1:2 to 1:11 in radioimmunoassay (RIA) diluent (see, Nicholson et al, *Clin. Chem.* 30, pg. 259, (1984)). The diluted samples were frozen and stored at −80° C. until assayed for ACTH. A control for degradation of ACTH over a three hour incubation period was conducted by adding known amounts of ACTH to cell-free wells and measuring the amount removed at 0.5, 1, and 3 hours. This control indicated that very little degradation occurs, suggesting that the ACTH measured in these experiments is representative of the ACTH secreted during the incubation period, independent of degradation.

(3) Radioimmunoassay (RIA): The assay was similar to methods used previously and described in Nicholson et al. ACTH standard, available from CIBA-Geigy of Basel, Switzerland, was diluted in RIA diluent to produce a standard curve ranging from either 0.5 pg/50 μl to 512 pg/50 μl or from 1 pg/50 μl to 1024 pg/50 μl. An anti-ACTH antiserum, a gift from C. Oliver of France, directed against the bioactive part of ACTH was used at a dilution of 1:28,000 or 1:25,000. A $^{125}$I-ACTH tracer was purchased from Radioassay Systems Labs of Carson, Calif. The total volume of each assay tube was 25 μl of antiserum, 25 μl of tracer and 50 μl of sample. Buffer blanks were included in all assays and indicated that the experimental medium did not interfere with the assay. Over twenty seven assays, the percent binding of $^{125}$I-ACTH tracer to antiserum of total counts was 31.4%±1.2% and the $r^2$ (correlation coefficient$^2$) of the log regression was 0.959±0.008.

(4) Peptides: All peptides used in the experiments were purchased from Peninsula Laboratories of Belmont, Calif. Rat ANF[1-28], rat ANF[5-28], and rat ANF[1-11] diluted by a ratio of 10 μg/100 μl in double distilled water and rat CRF 41 was reconstituted either in 0.1% acetic acid or 10 mM ascorbic acid. All peptides were stored at −80° C. until needed.

(5) Data Analysis: All data was collected as pg ACTH/50 μl of sample and converted to nanograms ACTH/well, accounting for the change in the volume of each well as sample was removed. Only experiments with a robust CRF effect (defined as greater than a two fold ACTH increase) were included in the analysis. For analysis, data was expressed as a fraction of the percent increase over baseline due to CRF 41 alone. Specifically, to obtain this value, the mean baseline was subtracted from all wells and the resulting number was divided by the mean baseline. The value computed for each group of wells was compared to the mean of those calculated for the wells receiving CRF 41 alone to obtain a relative CRF effect as shown in FIGS. 4, 5, and 6. This method of analysis was used to normalize the variable effects that CRF 41 had between experiments. Kruskal-Wallis analysis of variance by ranks was used to assess the significance of differences between groups. The time course data are expressed as a fraction of the mean pg ACTH/well at three hours due to CRF 41 alone. These data were statistically analyzed by Wilcoxon analysis of variance by ranks for repeated measures.

FIG. 1 illustrates a representative experiment for ANF[1-28] presenting data as ng ACTH/well. The first bar of each pair is the ng ACTH/well released during a three hour incubation during which all wells received experimental buffer. The second bar indicates the ACTH level induced by the indicated treatment. The concentration of CRF 41 used was 5 nM. The * indicates a probability ($p<0.05$), as calculated by Kruskal-Wallis ANOVA by ranks. The results show ANF-[1-28], at concentrations of 100 pM and 1000 pM, suppressed the stimulatory effect of CRF 41 by 51% and 54%, respectively.

FIG. 2 illustrates a representative experiment for ANF[5-28] presenting data in the same manner as shown in FIG. 1 and described above. The results show ANF[5-28] at concentrations of 100 pM, 1000 pM, and 10,000 pM did not suppress ACTH release.

FIG. 3 illustrates a representative experiment for ANF[1-11] presenting data in the same manner as shown in FIGS. 1 and 2 and described above, except that the pre-incubation with buffer was only one hour long. At concentrations of 100 pM and 1000 pM, ANF-[1-11] inhibited ACTH release by 37.3% and 33.6%, respectively. In the same experiment, 10,000 pM ANF-[1-11] increased ACTH release by 133.4%. The effects demonstrated in this experiment were not statistically significant.

FIG. 4 shows a dose-response curve for ANF[1-28] where the data are expressed as relative CRF effect as explained above. The data from fifteen different experiments, similar to the data shown in FIG. 1, has been combined to make the graph shown in FIG. 4. The CRF 41 concentration used varied from 1 nM 5 nM. The * indicates probability of $p < 0.05$ and the ** indicates a probability of $p < 0.001$ as determined by Kruskal-Wallis ANOVA by ranks. The results demonstrate that ANF[1-28], at 10 pM to 1000 pM, significantly inhibits CRF 41 stimulated ACTH release in vitro. ANF[1-28] at 100 pM concentration has the most potent inhibitory effects wherein the effectiveness of 1 to 5 nM CRF 41 to induce ACTH release was decreased by 40.1%. Concentrations lower than 10 pM were ineffective and 10,000 pM ANF[1-28] had less potent inhibitory effects that were not statistically significant.

FIG. 5 shows a dose-response curve for ANF[5-28] where the data are expressed as relative CRF effect as explained above. The data from six different experiments, similar to the data shown in FIG. 2, has been combined to make the graph shown in FIG. 5. The results show that ANF[5-28], at 10 pM to 10,000 pM does not alter ACTH release.

FIG. 6 shows a dose-response curve for ANF[1-11] where the data are expressed as relative CRF effect as explained above. The data from seven different experiments, similar to the data shown in FIG. 3, has been combined to make the graph shown in FIG. 6. The results show a trend for inhibition at concentrations from 10 pM to 1000 pM and stimulation at 10,000 pM. None of the points are statistically different from that for CRF 41 alone. When the effectiveness of equal concentrations of ANF[1-11] and ANF[5-28] were compared, the ACTH levels for 100 pM ANF[1-11] were significantly lower than those for 100 pM ANF[5-28].

FIG. 7 illustrates the time course for experiments with ANF[1-28]. All data is expressed as a fraction of the CRF effect after three hours of incubation. The data from four different experiments is included. The * indicates a probability ($p < 0.05$) as determined by Wilcoxon ANOVA by ranks for repeated measures. FIG. 7 shows that the inhibitory effects of ANF[1-28] were manifested only after three hours of incubation.

FIG. 8 illustrates the time course for experiments with ANF[5-28]. Data is expressed the same as in FIG. 7. The data from two experiments is included. FIG. 8 shows that ANF[5-28] does not affect CRF 41 stimulated ACTH release at each time point.

FIG. 9 illustrates the time course for experiments with ANF[1-11]. Data is expressed the same as in FIG. 7. The data from three experiments is included. FIG. 9 shows that ANF[1-11] did not significantly alter ACTH release after 0.5, 1, and 3 hours of incubation.

Table 1 shows the slopes of the lines between the 1 hour and 3 hour time points shown in FIGS. 7, 8, and 9.

TABLE 1

SLOPES OF RELATIVE CRF EFFECT BETWEEN 1 AND 3 HOURS

| ANF FORM | BASELINE | CRF ALONE | 100 pM ANF |
|---|---|---|---|
| | (MEANS ± SEM) | | |
| ANF[1-28] | .163 ± .032 | .249 ± .063 | .067 ± .045* |
| ANF[5-28] | .126 ± .026 | .324 ± .067 | .278 ± .055 |
| ANF[1-11] | .116 ± .024 | .275 ± .089 | .133 ± .059 |

Comparing the slopes presented in Table 1, the slope of the line for 100 pM ANF[1-28] is significantly less than that for CRF alone, while the slope of the line for 100 pM ANF[5-28] indicates that ACTH secretion is relatively unaffected by ANF[5-28]. The slope of the line for ANF[1-11] was 48.4% of that for CRF alone, although not statistically significantly different.

These experiments were designed to examine the effects of various molecular forms and concentrations of ANF on ACTH secretion by sustained application of CRF 41. ANF[1-28] at 10 pM to 1000 pM showed a pronounced inhibition of CRF 41 stimulated ACTH secretion. The absence of four amino acids from the N-terminal sequence of this peptide completely abolished the inhibitory effects. The C-terminal truncated ANF, ANF[1-11] was investigated and at 10 pM to 1000 pM concentrations, ACTH release was inhibited by a maximum of 23.7%, as shown in FIG. 6. The ANF-[1-11] inhibitory effects were not statistically significant, but the trends imply that the N-terminal sequence alone, without the ring structure, may have physiological effects. This is supported by the fact that ANF-[1-11] at 100 pM concentration does significantly decrease ACTH release when compared to 100 pM ANF-[5-28].

The U-shaped dose response curves for ANF[1-28] and ANF[1-11], shown in FIGS. 4 and 6, respectively, imply that there may be two types of ANF receptors with different binding affinities. This would be similar to those suggested in the adrenal cortex (see, Takayanagi et al, Biochem. Biophys. Res. Commun. 144, pg. 244, (1987)). Alternatively, at higher concentrations the ANF molecules could bind to each other and, thereby, interfere with interactions with the receptor.

The experiments demonstrate that ANF with an intact N-terminal, at low concentrations, and three hours of incubation are required to demonstrate inhibition of CRF stimulated ACTH release in culture. These requirements explain the failure of previous experiments to demonstrate inhibition of ACTH release, as well as the weak inhibitory effects of ANF[4-28]. Since physiological levels of ANF[1-28] are most effective at suppressing stimulation by amounts of CRF 41 similar to, or exceeding, those found in hypophyseal portal blood, it can be inferred that ANF[1-28] is a physiological inhibitor of ACTH release. ACTH is part of a large precursor protein, proopiomelanocortin. Many bioactive peptides, such as alpha-MSH, beta-MSH, beta-endorphin, and beta-LPH, are part of proopiomelanocortin and are released upon stimulation by CRF 41 in conjunction with the release of ACTH. In consequence, inhibition of ACTH release by ANF[1-28] or other ANF analogs with intact N-terminal sequences will cause inhibition of these peptides. Both cortisol, which is released in response to ACTH, and beta-endorphin have been shown to cause partial immunosuppression. Therefore, low doses of ANF analogs with intact N-terminal sequences should alleviate stress induced immunosuppression. The ANF analogs can be administered non-invasively by nasal inspiration, buccal application for intestinal absorption, by suppository, by injection or other means. The ANF analog may be modified to facilitate the absorption in the intestine.

In vivo, hormone factors are known to act together. Other known stimulators for inducing ACTH release include vasopressin, oxytocin, angiotensin II, and catecholamines. ACTH release resulting from combinations consisting of CRF 41 together with these other known stimulators will be inhibited by low concentrations of ANF or ANF-like peptides with intact N-terminal sequences.

While the invention has been described in terms of specific ANF peptides with intact N-terminal sequences, those skilled in the art will recognize that other ANF-like peptides with intact N-terminal sequences may be potent and stable inhibitors of CRF 41 induced ACTH secretions. Also, those skilled in the art will recognize that ANF analogs with intact N-terminal sequences may inhibit the ACTH secretion stimulated by combinations of CRF 41 or active analogs thereof together with other known stimulators for inducing ACTH release, such as vasopressin, oxytocin, angiotensin II, and catecholamines.

Having thus described my invention, what I claim as novel and desire to secure by Letters Patent is the following:

1. A method for suppressing corticotropin releasing factor 41 induced adrenocorticotropin hormone secretion from pituitary cells comprising the step of providing said pituitary cells with rat ANF[1–28] at a concentration ranging from 10 to 1000 picomolar or a pharmaceutically acceptable salt thereof.

* * * * *